United States Patent [19]

Weissman

[11] Patent Number: 4,729,736
[45] Date of Patent: Mar. 8, 1988

[54] CONTOURED DENTAL POSTS

[75] Inventor: Bernard Weissman, New York, N.Y.

[73] Assignee: IPCO Corporation, White Plains, N.Y.

[21] Appl. No.: 904,205

[22] Filed: Sep. 8, 1986

[51] Int. Cl.[4] .............................................. A61C 5/08
[52] U.S. Cl. .................................................... 433/221
[58] Field of Search ........................ 433/220, 221, 225

[56] References Cited

U.S. PATENT DOCUMENTS

| 313,737 | 3/1885 | How ........................................ 433/221 |
| 4,479,783 | 10/1984 | Weissman ............................ 433/221 |
| 4,571,187 | 2/1986 | Weissman ............................ 433/221 |

Primary Examiner—Robert Peshock
Attorney, Agent, or Firm—Helfgott & Karas

[57] ABSTRACT

A dental post for securely retaining a dental restoration on a prepared tooth stub. The dental post is formed of an elongated cylindrical pin having a longitudinal axis. Helical grooves are provided about the periphery of the pin for retaining the pin secured within a cement prepared bore within the tooth stub. An outer contour is formed along the longitudinal length of the pin to define annular retaining ledges axially spaced apart along the pin interspersed with inwardly tapered pin sections. The ledges serve to aid in the retention of the pin in the bore and increase the strength of the pin reducing the possibility of pin shear.

22 Claims, 8 Drawing Figures

CONTOURED DENTAL POSTS

BACKGROUND OF THE INVENTION

This invention relates to dental posts, and more particularly to a helically grooved dental post which includes a longitudinal contour to improve its retention within a prepared tooth stub on which a dental restoration will be erected.

In restoring dentition, one procedure is to build up a dental prosthetic structure onto a tooth stub. The tooth stub is initially prepared by cutting it down to provide a suitable support on which the prosthetic structure will be built. A bore is formed into the tooth stub in which a dental post is inserted. The dental post includes grooves thereabout for improving its retention in the bore formed in the tooth stub. Suitable dental cement is used for the retention. A portion of the dental post extends upwardly above the surface of the tooth stub so that as the dental prosthetic structure is formed or built up onto the tooth stub, it is retained in place on the tooth stub by means of the extending portion of the dental post.

Various types of grooves have been suggested in the prior art in order to improve the retention of the dental post within the cement prepared bore in the tooth stub. By way of example, there has been suggested to provide a helical thread about the periphery of the dental post. The inclusion of a longitudinal vent along the helical grooves permits escape of the air during insertion of the post and reduces the hydraulic pressure upon insertion. U.S. Pat. No. 4,268,253 describes a dental post having deep concave channels helically formed about the post to give the post a polygonal cross section. The use of helical flutes has been suggested in U.S. Pat. No. 4,479,783 assigned to the assignee of the present invention. Such helical flutes can be provided in a sequence with designated flutes being deeper than alternating shallower flutes. The use of such flutes can eliminate the need of the axial vent. Improvements in the retention capabilities of dental posts are also described in U.S. Pat. No. 4,571,187 assigned to the assignee of the present invention including an angled tang at the upper end of the post with projecting angular ribs about the tang to improve dental retention.

While the aforementioned dental posts have provided improvements with respect to the retention of the post in the bore, still further improvements in such retention would be beneficial. Additionally, the use of the helical grooves, flutes, and channels also provide a situation where the pin can bend or break along such indentations. Also, the grooves provide the possibility of shearing along length of the post.

SUMMARY OF THE INVENTION

Accordingly, it is an object of the present invention to provide an improved dental post.

A further object of the present invention is to provide a dental post having improved retention capabilities within a cement prepared bore within a tooth stub.

Still a further object of the present invention is to provide a dental post having a helically grooved periphery and a longitudinally contoured outer edge.

Still a further object of the present invention is to provide a dental post having a plurality of spaced apart ledges formed along the axial length of the post to provide improved retention within the cement in a bore of a tooth stub.

Another object of the present invention is to provide a dental post which has increased strength to avoid potential breaking or fracturing of the post along its length.

Yet a further object of the present invention is to provide a dental post which has greater resistance to dislocation of the post from the cement in a prepared bore in a tooth stub.

Another object of the present invention is to provide a dental post having helical grooves and annular ledges both of which are formed during a single rolling operation, which provides additional hardness to the dental post during the working of the post.

Briefly, in accordance with the present invention there is provided a dental post for securely retaining a dental restoration on a prepared tooth stub. The dental post includes an elongated cylindrical pin with an elongated longitudinal axis. Helical grooves are formed around the periphery of the pin for retaining the pin secured within a cement prepared bore in a tooth stub. An outer contour is longitudinally formed along the peripheral edge of the pin to define annular retaining ledges radially positioned about the pin and axially spaced along the length of the pin. These ledges further retain the pin secured within the bore and reduce the possibility of bending or breakage along shear lines of the pin.

In an embodiment of the invention, the helical grooves and the longitudinal contour are both formed during a rolling operation. Such rolling operation also serves to increase the strength of the dental post as a result of the work hardening process.

The aforementioned objects, features, and advantages of the invention, will, in part, be pointed out with particularity, and will, in part, become obvious from the following more detailed description of the invention taken, in part, with the drawing which form an integral part thereof.

DETAILED DESCRIPTION OF THE PREFERRED EMBODIMENT

Figure 1:
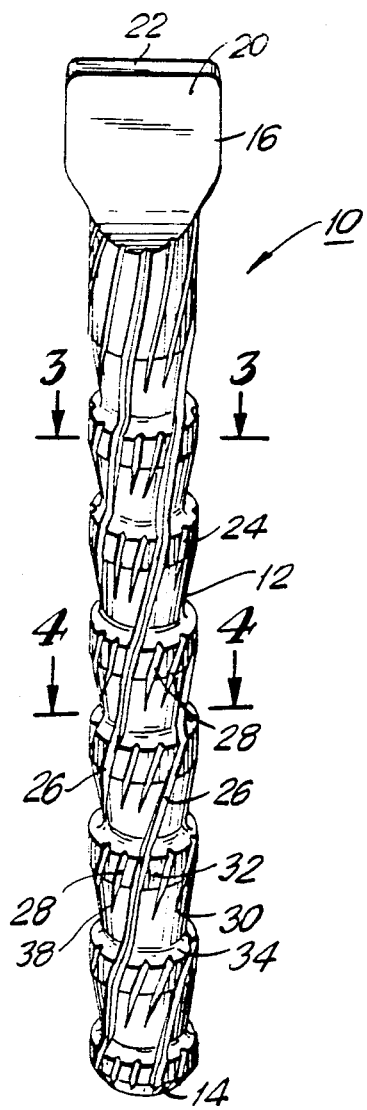
FIG. 1 is a perspective view of a dental post in accordance with the present invention.
Figure 2:
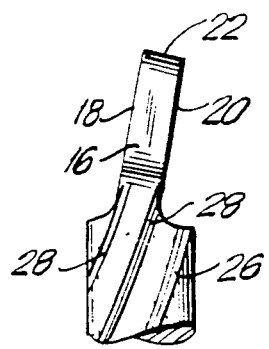
FIG. 2 is a side elevational view of the dental post shown in FIG. 1 and specifically showing the angular orientation of the tang portion at the head of the post.

Referring now to the drawings, the dental post of the present invention is shown generally at 10 and comprises a cylindrical pin 12 having substantially flat lower end 14 and a flattened, angularly oriented tang 16 at its upper end. The tang portion includes opposing faces 18, 20 which project axially beyond the upper end of the cylindrical pin portion. The upper edge 22 is flattened. On each of the facing portions 18, 20 there could be included suitable indicia identifying the pin or its material. Furthermore, peripheral ribs could be included in order to further enhance the retention capability of the dental restoration on the pin as is described in the aforementioned U.S. pat. No. 4,571,187.

The pin itself is provided with multiple helical grooves 24 which wind helically about the periphery of the pin. These grooves are typically flutes, of the type described in the aforementioned U.S. Pat. No. 4,479,783. As is therein described, certain of the flutes 26 are deeper flutes and are interspersed with shallower flutes 28. The flutes can be of the aforementioned type in which case the pitch of the flutes is greater than the length of the pin so that a separate spiral path of each of the flutes is less than one revolution about the pin. The flutes can be provided with a pitch angle of less than 10° degrees with respect to the longitudinal axis of the pin.

As a result of the multiple flute lines that terminate at the bottom 14, as the lower end 14 is inserted into the tooth bore, there are a plurality of flute lines for escape of the air in the bore. The hydrostatic pressure can therefore be reduced as the air escapes along the multiple flute lines each of which provide a separate venting path. Also, there is no blocking wall facing the insertion direction. As a result, the pin can be fully seated with the first insertion effort without having the build up of hydrostatic pressure in the bore, thus avoiding the pushing out of the post.

The grooves or flute lines, 26, 28 provide retention of the dental post in the cement prepared tooth bore. Specifically, the cement itself lodges within the V-shaped grooves or flute lines and retains the post in place. By way of example, there is shown to be provided two smaller grooves 28 between each pair of larger grooves 26. However, it should be appreciated that other arrangements could also be utilized.

Figure 5:
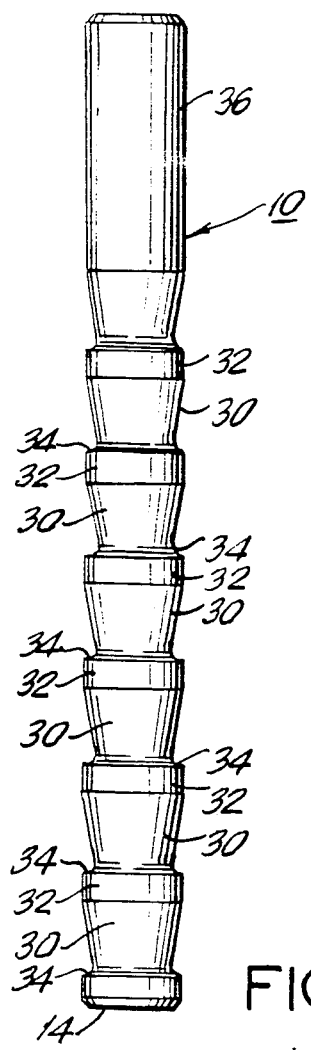
FIG. 5 is an elevational view showing the post with just its longitudinal contour along the periphery of the post.

In addition to the grooved arrangement, the post 10 also has an axial contour along its entire length. The contour can be better noted in FIG. 5 where the contour is shown without the presence of the grooves or flutes. As can best be noted in FIG. 5, the peripheral contour is such to provide a plurality of inwardly tapered sections 30 interspaced by angular bands 32. At the lower end of the tapered sections 30, at their junction with the englarged bands 32 there are provided substantially radial shoulder portions or ledges 34. These ledges 34 are annular and are uniformally spaced apart along the entire axial length of the pin 10. The upper end 36 as shown in FIG. 5 shows the initial cylindrical pin portion prior to its being flattened and angularly bent into the tang shown on FIG. 1.

Figure 3:
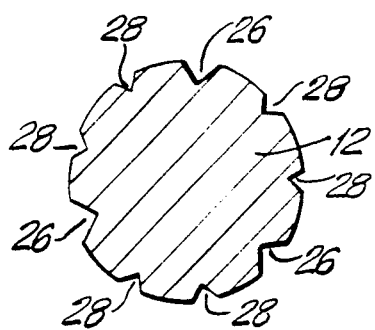
FIG. 3 is a cross sectional view taken along lines 3—3 of FIG. 1 and showing the helical grooves at a crest or maximum diameter position along the length of the post.
Figure 4:
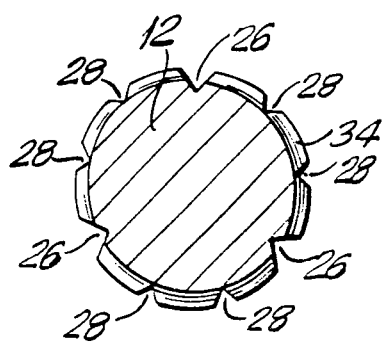
FIG. 4 is a cross sectional view taken along lines 4—4 of FIG. 1 and showing the helical grooves at a valley or minimal diameter portion along the length of the post.

The depth of the grooves is such that the depth of the larger grooves 26 is greater than the radial width of the annular shelf or ledge 34. On the other hand, the depth of the shallower grooves 28 is less than the radial width of the annular shelf or ledge 34. As a result, as is shown in FIGS. 1, 3, and 4, the larger grooves or flutes 26 extend entirely around the periphery along both the wider bands 32 as well as across the tapering sections 30. On the other other hand, the depth of the shallower grooves 28 is less than the radial length of the annular ledge so that it tends to fade or disappear along the tapering portion 30. As shown in FIG. 1, the edge of the shallow groove 28 terminates at a point 38 somewhere along the length of the tapered section 30.

The presence of the larger flutes or grooves 26 which continue intact throughout the entire length of the pin provide the necessary venting which is needed for the release of the hydrostatic pressures upon insertion. The shallower grooves provide retention benefit for holding the cement imbedded within the body of the pin.

The presence of the shelves or ledges 34 are significant in improving the torgue resistance to dislocation of the pin within the cement prepared bore. In use of the grooves alone, there is provided a limited amount of cement which is imbedded along the length of the post. The ledges provide for deep axial lengths of cement sections which are provided as blocks around the periphery of the post to further secure it in place. Tests on the post of the present invention have shown a substantial increase in retention strength of the post within the cement prepared bore.

In addition, the post of the present invention has reduced chances of bending or breaking. With the presence of helical grooves, there are created shear points about the post. In fact, each groove can be a shearing point for the post. By including a peripheral elongated contour as in the present invention, there is a reduction in the bending or breaking instances of the post. There are less notches around the periphery forming a reduction in the possibility of shearing and at the same time there is an increase in the retention capability.

In one method of manufacture, the elongated contour is formed in a rolling process. The helical flutes or grooves can be likewise formed in a rolling process. In fact, the best embodiment thus far found for the manufacture of the post is where the grooves as well as the elongated contour are both formed in the same rolling process. In such case, the initial cylindrical pin forms the stock which passes through the rolling process and both the helical grooves and the annular shelves are formed.

During the formation, the axial length of the pin is slightly increased as the elongated contour is formed. At the same time, the pin increases in hardness as a result of the work hardening process.

The increase in the strength of the post as a result of the manufacture process, the increase in the retention capability because of the presence of the shelves, and the reduction in the shearing points along the length of the post provide substantial improvement in the effective use of the post.

Figure 6:
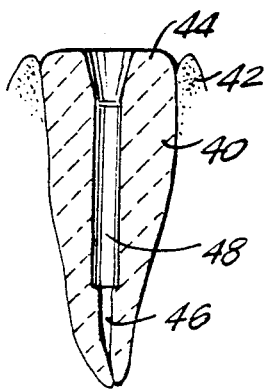
FIG. 6 is a cross sectional view taken through a tooth stub showing the preparation of the tooth stub for utilization of the dental post of the present invention.
Figure 7:
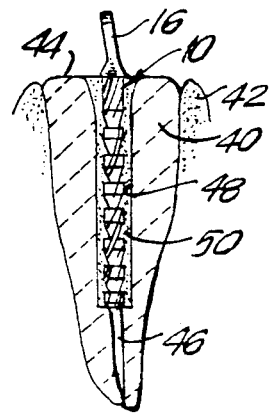
FIG. 7 is a cross sectional view similar to that shown in FIG. 6 and showing the inserted dental post of the present invention within the cement prepared bore of the tooth stub.
Figure 8:
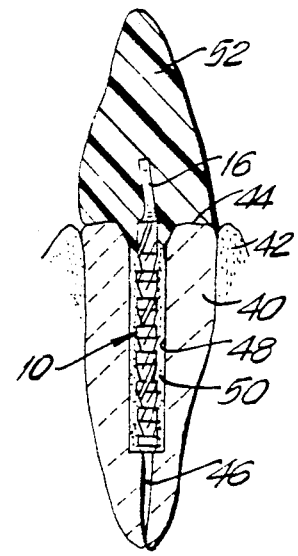
FIG. 8 is a view similar to that shown in FIG. 7 and including the dental restoration placed upon the tooth stub.

Referring to FIGS. 6-8, the method utilizing the present dental post 10 will be briefly described. By way of example, there is shown a tooth stub 40 within the gum area 42, where the upper end of the tooth has been broken. The tooth has been initially cut down, typically to provide a suitable upper surface 44. In order to build up a super structure onto the tooth stub 40, there is required a retaining member, such as the dental post of the present invention.

Initially, conventional root canal work is carried out by drilling and cleaning out of the pulp along the canal section 46 provided in a tooth stub. Subsequently, an enlarged bore 48 is drilled into the tooth of a size commensurate with the periphery of the dental post to be inserted. Cement 50 is then placed into the bore 48 and onto the dental post 10 which is then inserted into the bore 48. The cement fills the flutes or grooves around the periphery of the pin. Additionally, it fills in the ledges or shelves radially positioned along the length of the pin. This substantially improves the retention capability of the pin within the tooth stub.

The upper end tang 16 of the post 10 extends upwardly above the surface 44 of the tooth stub. A superstructure 52 can then be suitably formed onto the tooth stub in accordance with standard well known techniques in the dental line. The superstructure 52 is retained onto the upper end 16 of the dental post 10 and remains securely in place thereby.

There has been described heretofore the best embodiment of the invention presently contemplated. However, it is to be understood that various changes and modifications may be made thereto without departing from the spirit of the invention.

What is claimed is:

1. A dental post for securely retaining a dental restoration on a prepared tooth stub, comprising:
   an elongated cylindrical pin having a longitudinal axis;
   helical grooves disposed about the periphery of said pin for retaining said pin secured within a cement prepared bore in a tooth stub; and
   an outer contour longitudinally formed into the periphery of the pin to define annular retaining troughs about the pin to further retain said pin secured within the bore.

2. A dental post as in claim 1, wherein said troughs are uniformly spaced apart along the length of the pin.

3. A dental post as in claim 1, wherein said troughs terminate in inwardly tapered pin sections along the length of the pin.

4. A dental post as in claim 1, wherein at least some of the grooves have a depth less than the depth of the troughs.

5. A dental post for securely retaining a dental restoration on a prepared tooth stub, comprising:
   an elongated cylindrical pin having a longitudinal axis;
   helical grooves disposed about the periphery of said pin for retaining said pin secured within a cement prepared bore in a tooth stub;
   an outer contour longitudinally formed into the periphery of the pin to define annular retaining troughs about the pin to further retain said pin secured within the bore. And comprising
   a first group of grooves having a depth greater than the depth of the troughs and a second group of grooves alternating in sequence with the first group of grooves and having a depth less than depth of the troughs.

6. A dental post as in claim 1, and further comprising a head portion extending from said pin for projecting outwardly from the tooth stub upon which the dental restoration can be secured when said pin is inserted into the tooth stub bore.

7. A dental post as in claim 1, wherein said head portion comprises a flattened tang integral with said pin.

8. A dental post as in claim 7, wherein said tang is angularly oriented with respect to the pin axis.

9. A dental post for securely retaining a dental restoration on a prepared tooth stub, comprising: an elongated pin for securement within the tooth stub and comprising a plurality of longitudinally tapered sections, annular, radially extending shoulder portions separating adjacent sections, and helical grooves disposed about the periphery of the pin.

10. A dental post as in claim 9, wherein said shoulder portions include cylindrical bands at the upper ends of each section.

11. A dental post as in claim 10, wherein said cylindrical bands conform to the outer peripheral edge of the pin.

12. A dental post as in claim 11, wherein at least some of said grooves penetrate said cylindrical bands.

13. A dental post as in claim 11, wherein at least some of said grooves fade out along the tapered sections.

14. A dental post for anchoring a prosthetic device, comprising: a head on which said device may be mounted, and a shaft extending therefrom for insertion into a previously prepared bore for securement therein by cement, said shaft including a plurality of longitudinally spaced apart reduced diameter annular throat sections, and helical grooves disposed about the periphery of said shaft, said grooves and throat sections retaining said shaft secured within the cement.

15. A dental post as in claim 14, and further comprising inwardly tapered shaft sections extending between adjacent throat sections.

16. A dental post as in claim 14, wherein said shaft has a first diameter, said throat sections having a second diameter less than said first diameter, and wherein said shaft terminates at a lower free end having a diameter substantially equal to said first diameter.

17. A dental post as in claim 14, wherein at least some of said grooves have a depth less than said reduced diameter.

18. A dental post as in claim 14, wherein said throat sections are uniformly spaced along said shaft.

19. A dental post for securely retaining a dental prosthesis on a prepared tooth stub, comprising: an elongated pin for securement within the tooth stub and comprising a longitudinal ratchet surface having portons tapering toward an insertion end and formed peripherally about said pin for one way insertion into the tooth stub, and helical grooves disposed about the periphery of the pin for retaining the pin secured within the cement.

20. A dental post as in claim 19, wherein said ratchet surface comprises inwardly angled cylindrical pin sections terminating in radially outwardly oriented ledges.

21. A dental post for securely retaining a dental prosthesis on a prepared tooth stub, comprising: an elongated pin having an outer diameter for securement within the tooth stub, elongated sections of reduced diameter spaced along the pin, annular bands of pin sections of a diameter approximating the outer pin diameter, and separating said elongated sections, and helical grooves disposed about said pin for retaining the pin secured in the tooth stub.

22. A dental post as in claim 21, wherein said grooves extend along said annular band.

* * * * *